United States Patent [19]

Venegas

[11] 4,155,356
[45] May 22, 1979

[54] RESPIRATION ASSISTING APPARATUS AND METHOD

[76] Inventor: Jose G. Venegas, Apartado Aereo No. 90079, Bogota, Colombia

[21] Appl. No.: 764,865

[22] Filed: Feb. 2, 1977

[30] Foreign Application Priority Data

Feb. 10, 1976 [GB] United Kingdom ............... 5241/76

[51] Int. Cl.² ............................................. A61M 16/00
[52] U.S. Cl. ................................ 128/145.6; 128/184; 128/38
[58] Field of Search ............... 128/145.6, 145.5, 145.7, 128/145.8, 142, 38, 39, 40, 28, 184, 2.06 R, 2 R

[56] References Cited

U.S. PATENT DOCUMENTS

| | | | |
|---|---|---|---|
| 2,918,917 | 12/1959 | Emerson | 128/145.6 |
| 3,349,766 | 10/1967 | Donofrio | 128/145.6 |
| 3,863,082 | 1/1975 | Gillott et al. | 128/145.6 X |
| 3,923,055 | 12/1975 | Hammacher | 128/DIG. 17 |
| 3,993,059 | 11/1976 | Sjostrand | 128/145.8 |

FOREIGN PATENT DOCUMENTS

355416   6/1922   Fed. Rep. of Germany ........ 128/145.6

OTHER PUBLICATIONS

Weinstein, "A Method for Re-expansion of the Collapsed Lung" in Early or Late Empyema, Aug. 1936, vol. 28, #3, Industrial Engr.

Primary Examiner—Henry J. Recla
Attorney, Agent, or Firm—Kenway & Jenney

[57] ABSTRACT

Process and apparatus for assisting expiration of respiratory gas from the lungs and/or assisting pulmonary blood circulation. The apparatus comprises means for generating a series of pressure pulses and means for transmitting the pressure pulses to air passageways in the lungs through respiratory gas. The generating means can comprise a solenoid controlled pump, a solenoid controlled valve, or a reflector means for directing pulses into the lungs. The transmitting means preferable comprises a tube for placement in the trachea. The frequency, amplitude, and shape of the pressure waves are controlled to outwardly displace walls of collapsed air passageways in the lungs, to maintain the outward displacement, and to generate a pumping action to assist in respiration. Wave characteristics may be controlled manually or modulated by signals derived from an electrocardiogram and/or a pleural pressure sensing means.

29 Claims, 9 Drawing Figures

RESPIRATION ASSISTING APPARATUS AND METHOD

BACKGROUND OF THE INVENTION

This invention relates to a remedial apparatus for use in assisting the breathing of living creatures, and more particularly, to an apparatus useful in cases where the passage of air or other gas to be inspired or expired is obstructed by the inward displacement or collapse of passageway walls of the respiratory system. Such collapse produces uneven distribution of gases through the lungs and affects not only the bulk of gas flow through the airways of the system but also the entire gas exchange process.

For convenience in the following description, reference will be made to the application of the apparatus to human beings. However, it will be understood that suitable forms of the apparatus may be applied to other living creatures. Further, also for convenience, reference will be made to air as the respiratory gas. However, it will be understood that the apparatus may be used with other respiratory gases, for example oxygen and those used in anaesthesia.

For practical purposes, the human respiratory system may be considered as a complex network of visco-elastic tubes branching continuously in decreasing diameter, length, and wall thickness. The different levels are indicated as generations with the trachea as the first, the main bronchi as the second, and so on down to the alveolar sacs as the twenty-third. The trachea and main bronchi are supported by U-shaped cartilages which are joined posteriorly by smooth muscle bands.

Lobar and segmental bronchi (2–4 generation) have fairly firm cartilaginous support in their walls, initially in the form of irregularly shaped plates, and lower down, in the form of helical plates. The small bronchi (5–11 generation) extend through 7 generations with their diameter following from 3.5 to 1 mm. These have no cartilaginous structure.

From the bronchioles until the alveolar sacs (the smallest terminal compartments), the lung paracheyma structure may be represented as randomly oriented flat membranes (septa). In the normal lung, the paracheyma is alwayys in a pre-stretched condition. This creates a sub-atmospheric pressure in the outer surface of the lungs referred to as pleural pressure (Ppl) which maintains the structure expanded. When there is no air flow through the airways, the air pressure within the lungs is constant at all points and the pressure difference across any interior membrane is zero. However, because these membranes are stretched during deformation, a stress exists within them. Lung recoil is due partially to this elastic stretching of the lung paracheyma and partially to surface tension acting throughout the air-fluid interface lining the alveolar sacs.

Alveolar pressure (Palv) is the driving pressure which causes air to flow through the airway in and out of the lungs. To a close approximation, Palv may be considered as made up of two parts; the pleural pressure (Ppl) and the lungs recoil pressure (Pst) so that:

$$Palv = Ppl + Pst$$

Pst is always positive in sign with respect to the atmospheric pressure and its value is proportional to the lung volume. Ppl is negative for all inspirations and most expirations. During forced expirations, however, Ppl becomes positive in sign due to activity of expiratory muscles. Because Palv is the total pressure drop between the alveoli and the mouth (atmosphere), there is a point within the airways at which the pressure of the air at the inner walls equals Ppl.

At this pressure, Ppl is also the external pressure applied on the airway, the transmural pressure between the inside and the outside of the airway wall will be negative at all points downstream of this point. If the transmural pressure difference is sufficiently strong to overcome the rigidity of the airway, then the bronchi will necessarily collapse.

The above analysis explains why, with a constant lung volume, expiratory flow increases as driving pressure is increased until a critical level is reached and further increase in driving pressure does not result in any increase in expiratory flow.

It has been demonstrated that emphysematous patients exhibiting marked decrease in maximum expiratory flows generate their maximum flows even during quiet breathing. Accordingly, limitation of airflow rate by bronchial collapse is much more marked in such patients. Three combined factors are responsible:

(a) The resistance in the small bronchi of such patients is higher, and therefore the pressure drops more rapidly from the alveoli to the larger bronchi;

(b) The bronchi of an amphysematous person are less able to withstand collapse; and (c) The recoil pressure in each compartment, (calculated as $P = 2T/r$ where T is the elastic tension of the walls and r is the average radius), is reduced because, with the loss of septa, the average radius of the compartments increases.

The above atrophic changes are irreversible and usually progressive. Generally, some respiratory parameters are changed by the chronic obstructive lung disease patient in order to adapt his respiration to his pathologic condition. Firstly, his functional residual capacity (minimum lung volume during quiet breathing) is increased giving rise to the so called barrel chest. By this adjustment, he increases the average diameter of the ducts and the elastic recoil of the lung when the lung is expanded. Bronchial collapse is thereby reduced.

Secondly, the patient learns to increase the expiratory resistance of his upper airways by grunting or pursed-lip breathing. This increase in resistance gives rise to an increase in tracheal pressure which in turn reduces to some extent airway collapse and air trapping in those zones affected by the disease. Nevertheless, pursed-lip breathing also increases the effort requiredn during breathing and leads to a higher oxygen consumption.

Thirdly, the patient tries to avoid making forced expirations such as coughing. The ineffectiveness of the effort can often be more distressing than the limitations of ventilation.

In extreme cases, or during anaesthesia, artificial respiration is used in Chronical Obstructive Lung Disease (C.O.L.D.) patients. Problems of airtrapping and poor gas exchange are frequently encountered in dealing with those patients.

It is one object of this invention to provide an apparatus for increasing airflow during expiration by avoiding or reducing obstruction arising from inward displacement or collapse of the walls of the air passageways.

Another object of the invention is to provide a process for assisting expiration of respiratory gas from the lungs especially but not exclusively during anaesthesia procedures.

Another object of the invention is to provide an apparatus for assisting air flow during expiration by maintaining an outwardly displaced position of gas passageways in the lungs.

Another object of the invention is to improve gas mixing and blood circulation in the lungs.

SUMMARY OF THE INVENTION

According to the invention, there is provided a remedial apparatus and process for use in assisting the breathing and/or the pulmonary blood circulation of living creatures. In its broadest aspects, the apparatus comprises a means for repetitively generating pressure pulses or waves in air or other respiratory gas of a magnitude, frequency (e.g. 15 Hz), and envelope (represented graphically by pressure plotted against time) such as to be effective at the site of an obstruction to provide outward displacement of an inwardly displaced or collapsed air passageway wall, and a transmission means for feeding the pressure pulses to a station, so situated relative to the subject, that pulses travel upstream of the air passageway to the site of the obstruction.

While it is within the scope of the invention for the transmitting means to comprise a room, cubicle, or other enclosure for accommodating the subject or subjects concerned so that such pressure pulses are incident (at large) at the mouths and/or nasal passageway outlets of the subject or subjects, the preferred form of transmission means is a duct of a size such that it can be introduced into the mouth or trachea, or preferably, coupled to the bronchial passage. Such duct may afford sufficient internal clearance for inspiration or expiration otherwise than through such duct, or the whole of the flow of air or gas may take place through such duct.

The duct is preferably formed of a nonmetallic flexible material, so dimensioned as to have physical characteristics compatible with the transmission of the pressure pulses to the air passageways of the subject from the termination of the duct without severe impedance mismatch and energy loss.

The apparatus may include means for applying an artificial ventilation (respiration) to the subject. Thus, in one embodiment, the duct forming the transmission means comprises a main duct connected or adapted for connection to a pressure pulse generator means, and a branch duct connected or adapted for connection to an artificial respiration means.

The geometry of the branch duct relative to the main duct may be such as to prevent or inhibit transmission of pressure pulses therealong to the artificial ventilation means, and restrictor means or valve means may be provided in association with the branch duct to assist in or effect such prevention or inhibition.

The pressure pulse generator means may include pump means, operable cyclically to produce the pressure pulses, or alternatively may include a reservoir or pressurized air or respiratory gas releasable by cyclically operable valve means. Alternatively, the source of air or respiratory gas may be that expired by the patient and the generator may comprise an exhaled gas reflector which is moved cyclically to generate the pulses. The pulse generator means may include electrical signal source means and means for generating pressure pulses having respective envelopes of which the slope of the leading or rising edge differs from that of the trailing or falling edge. In this regard, sound waves characterized by a relatively rapid rise in pressure followed by a relatively gradual decrease in pressure are contemplated. Acoustic means including an electromagnetic transducer and a diaphragm actuated by the transducer, for example, can be controlled by the electrical signal source means which generates a sawtooth electrical waveform having relatively steep portions separated by relatively gradual portions. The pulse generator means may also include means for controllably varying the shape of the pulse envelopes.

Preferably, the pulse generator means includes means for adjusting the repetition frequency of the pulses within a range such that each newly generated pulse is developed before inward displacement or collapse of the gas passageway wall of the subject can recur, after having been displaced outwardly by the preceding pulse. Thus, for human beings, it is contemplated that the pulse generating means should have a range of pulse repetition frequency covering at least the frequency band of one to thirty Hertz.

The pressure pulse generator means may further include control means for controlling or acting on the train of pulses in response to an input control signal developed by a means for sensing cardiac rhythm. Thus, it is contemplated that the pulse train may be amplitude modulated as a function of such input control signal. Alternatively, the input control signal may be used to gate or otherwise control the times over which pulses or pulse groups collectively forming the pulse train are generated.

The pressure pulse generator means may further include control means for providing an alternative or further input control signal for controlling or acting on the train of pulses in response to an input control signal developed by a means for sensing pleural pressure (Ppl.). Thus, the pulse train may be amplitude modulated as a function of this control signal. The sensing means may be in the form of a balloon for placement in, e.g., the intraesophageal region.

When using artificial positive pressure respiration on a patient, the high alveolar gas pressure produced by the machine increases the hydraulic resistance to blood flow in the pulmonary circulation system and can even collapse the small pulmonary veins. This is because the pulmonary circulation system is a low pressure circuit. (Pulmonary arterial pressure varies between 22 and 8 mm Hg). Under these circumstances, the heart has to work harder in order to supply the appropriate amount of blood to the rest of the body.

Because positive pressure respiration must be used in many patients, one should try to minimize the interference produced by the respiratory system on the pulmonary blood circulation. This can be achieved in accordance with the invention by superimposing an additional higher frequency pulsating pressure wave which is triggered by cardiac activity on the low frequency pressure output of a conventional positive pressure respirator. The phase relationship between this additional air pressure wave and the electrical heart signal must be such that when the blood pressure in the pulmonary capillaries is decreasing, the intra alveolar air pressure is high so that blood in the pulmonary veins is pumped towards the heart as the veins collapse. Furthermore, when the heart is forcing the blood through the pulmonary system, the intra alveolar air pressure remains low, thus reducing the resistance to blood flow as the veins will not be collapsed.

Accordingly, because this method reduces the instantaneous net resistance to blood flow, it is also useful in patients with pulmonary blood hypertension due to valvular stenosis or any type of increased resistance of the pulmonary blood circuit.

A further aspect of the invention resides in a method of remedying inward displacement or collapse of the wall of an air passageway of the respiratory system of a living creature comprising generating a series of pressure pulses in air or other respiratory gas of a magnitude, frequency, and envelope, such as to be effective at the site of an obstruction to produce outward displacement of the inwardly displaced or collapsed air passageway wall, and delivering such pulses to a station from which the pulses travel upstream along the flow path of the expired air or gas to be incident at the obstruction.

In addition to improving the bulk gas flow, the invention also improves gas mixing and blood circulation by avoiding or reducing the adverse effects on the gas exchange process which would otherwise occur.

BRIEF DESCRIPTION OF THE DRAWING

The invention will now be described, by way of example, with reference to several embodiments illustrated in the drawing therein.

Corresponding reference characters in the several drawings indicate corresponding parts.

DESCRIPTION OF THE PREFERRED EMBODIMENTS

Figure 1:
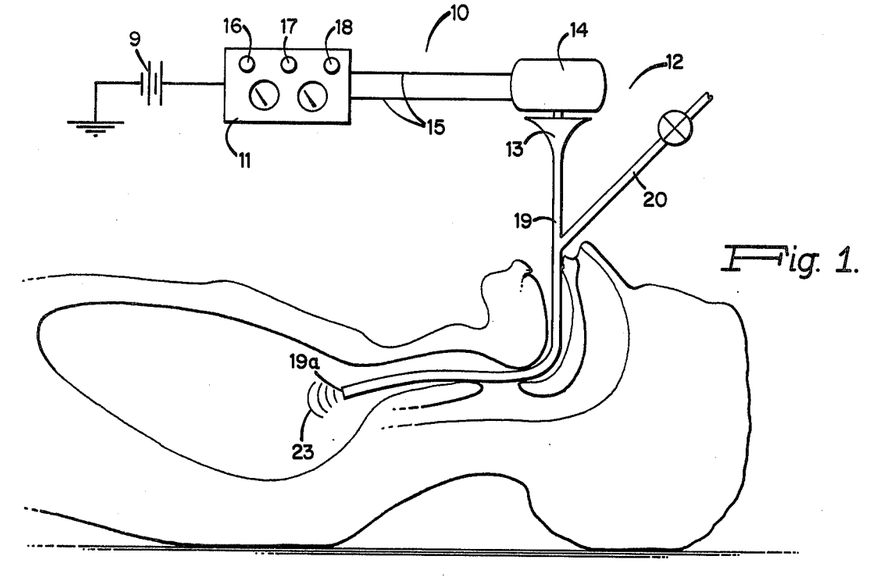
FIG. 1 illustrates a first embodiment of the invention in which the frequency and amplitude of the pressure pulses are controlled manually.

Referring to FIG. 1, the apparatus comprises a pulse generating means indicated generally at 10 which includes an electrical unit 11 powered from any suitable current source 9 which may be a battery or a main electrical supply, and further comprises what may be broadly termed transducer means 12 for converting the electrical pulses into pressure pulses in air. The transducer means comprises a pump 13 which may be a diaphragm pump as hereinafter described and a driving solenoid 14 which is energized by electrical current supplied through conductors 15 from the unit 11.

The unit 11 includes controls 16, 17, and 18 which are manually operable to control respective parameters of the series of electrical pulses furnished from the circuit. These parameters maybe the amplitude of each pulse developed, the repetition frequency of the pulses, the phase of the pulses, and a pulse shape parameter such as the slope of the leading or rising edge of each pulse. It will be understood that other parameters may be controlled such as the mark/space ratio.

The pump 13 has an outlet connected to a duct 19 for delivering the pressure pulses to a suitable site such that the pulses can travel upstream of the air flow path along which air is expelled by the patient. As shown, the duct 19 may be in the form of a flexible tube of a suitable material such as a plastic material which will withstand sterilization and is itself chemically inert so as to be unaffected by introduction into the patient's respiratory system. Typically, the duct 19 is introduced into the trachea.

Connected to the duct 19 is a branch duct 20 in fluid communication with an artificial respiration means 24. The duct 20 may contain a resistor means 22 which furnishes a variable pneumatic resistance and can be either preset or varied during operation as required.

Pressure pulses developed by operation of the pump 13 travel upstream in the duct 19 and are incident at the outlet 19a thereof in the patient's trachea. Thereafter the pulses travel upstream as indicated diagrammatically by the wave fronts 23. Should any of the air passageways along which these pulses continue to travel upstream present an obstruction by inward displacement or collapse of the side walls of the air passageway, the arrival of the wave front of a pressure pulse will locally and temporarily raise the internal pressure. This causes the inwardly displaced or collapsed side wall to be restored to a normal position. An interval of time will elapse before there is any renewed inward displacement or collapse of the side wall, the interval being dependent upon the physical characteristics of the side wall itself and the muscular breathing exertions of the patient. The frequency of the generated pulses is controlled so that the next pressure pulse wave front arrives at the obstruction just at the beginning of inward displacement. Accordingly, a further state of local raised pressure in the air passageway is created and such inward displacement is prevented. In this way, the outwardly displaced position of the air passageway is maintained.

The pressure increment represented by the pressure pulse will in general be a fraction of the pleural pressure (Pp1), and for optimum results, should be increased approximately linearly as the value of Pp1 rises.

The upstream travel of the pressure pulses does not prevent the expiration of air through the air passageways to the trachea. Expired air passes through branch duct 20 to an outlet.

The restrictor means 22 is set to a value such as to prevent or inhibit the transmission of pressure pulses therebeyond. This condition may also be assisted or, in some cases, established, without the use of a restrictor element merely by the geometry defined by the junction of the branch duct 20 with the main duct 19, where it will be observed that the ducts are in Y formation with the branch duct 20 joining the main duct 19 at an acute angle with respect to the part of the main duct 19 extending between the branch 20 and the pump 13.

The application of the pressure pulses, herein called reversed pressure pulses (R.P.P.), may be applied continuously to patients with severe chronic obstructive respiratory diseases, thereby allowing free flow of air or respiratory gas during expiration. Such pulses may, however, be applied periodically in cases where regions of air passageway collapse occasionally produce air trapping.

Coughing is only productive (i.e. gives relief) if secretions in the smaller air passageways are brought to major air passageways for expulsion by the explosive cough. Secretions cannot be so moved unless there is a flow of air or respiratory gas in these smaller air passageways which does not occur during forced expiratory effort (i.e., muscular exertion by the patient).

The present apparatus may be used to release blockage at positions in the air passageways where secretions are causing an obstruction.

Figure 2:
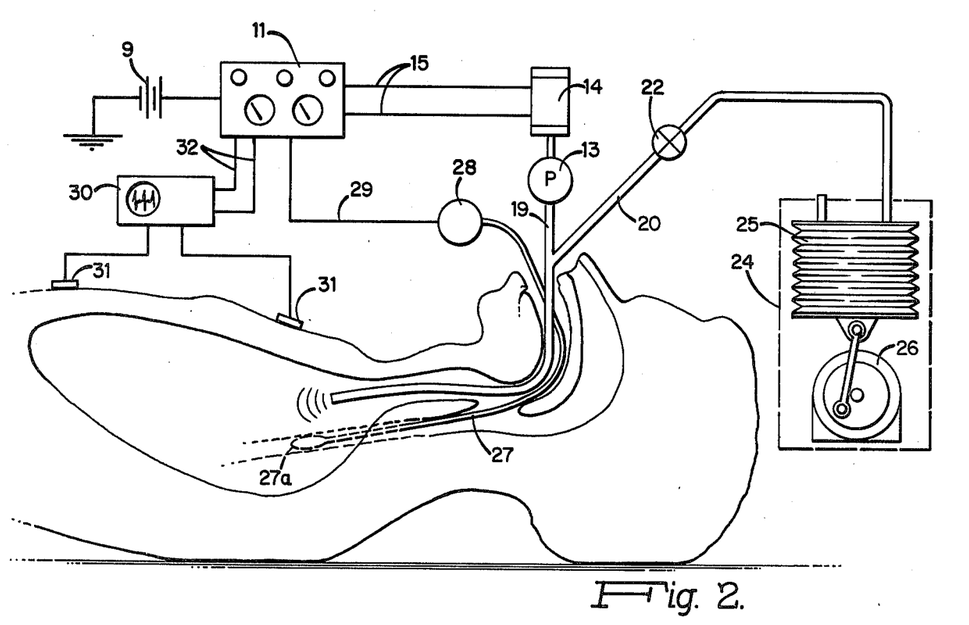
FIG. 2 illustrates the embodiment of FIG. 1 modified to include means for controlling the amplitude of the pulses as a function of intra-pleural pressure of the patient, means for controlling the frequency and phase of the pulses as a function of cardiac rhythm of the patient, and artificial respiration means.

In the modification of apparatus illustrated in FIG. 2, instead of controlling parameters of the series of electrical pulses generated by the unit 11 manually as by means of the controls 16, 17, and 18, additional control is provided by means 27 for sensing plural pressure (Ppl). Such means 27 may be in the form of an intraoesophageal balloon 27a. The pressure signals developed in the balloon are applied to the input of a pressure transducer 28 which feeds an electrical signal along conductor 29 to the circuit of the pulse generator 11.

It has been found that the amplitude of the pressure pulse which produces optimum increase in air flow through an air passageway with an inwardly displaced or collapsed wall is directly related to the external pressure (Ppl) acting over the tube. Because this pressure varies during expiration, it is desirable to control the amplitude of the pressure pulses delivered from the pump 13 as a function of the output of the transducer 28. Connection is made from the conductor 29 to a suitable point in the circuit of the unit 11 to control the amplitude of the electrical signals delivered along the lines 15.

Artificial respiration means 24 is shown diagrammatically attached to resistor means 22. It comprises a bellows 25 operated by an eccentric element 26 such as a crank driven by an electric motor operating at a speed correlated to the normal respiratory cycle of the patient. It will be understood that artifical respiration means 24 may be eliminated and branch duct 20 may simply be open to the atmosphere at a point beyond restrictor means 22 such as is shown in FIG. 1.

In addition to the plural pressure sensing means and artificial respiration apparatus. FIG. 2 illustrates a means for sensing cardiac rhythm comprising an electro-cardiagram unit 30 having sensing elements 31 supplied and maintained in contact with suitable external parts of the patient's chest to develop electrical signals representative of cardiac rhythm. These signals are amplified in the unit 30 and conveyed along conductors 32 to the unit 11.

The signals developed in the conductors 32 are applied to a suitable point in the circuit of the unit 11 to act on or control in a predetermined manner some characteristic of the pulse train. Typically, the pulse repetition rate of the train of pulses may be 15 Hz., and the repetition rate of cardiac signals may be 1 to 2 Hz. The latter signals may be fed to a circuit which develops a sine wave or similar continuous, cyclically varying signal having a fundamental frequency equal or related in some simple manner to that of the cardiac signals. This sine wave or similar signal may be used to modulate the pulse train to vary the amplitude of the pulses so that these rise to a maximum at the time at which the cardiac signals are developed (or in some predetermined phase relation thereto to obtain optimum results). Alternatively, the sine or similar wave developed from the cardiac signal may be used to gate or control the incidence of pulses in the train so that one such pulse, or a group of pulses, occur at the same time as a cardiac signal (or in some predetermined phase relationship thereto to obtain optimum results). Incidence of pressure pulses concurrently or in the selected phase relationship with cardiac signals produce a pumping effect with respect to small pulmonary vessels of the patient giving an extra impulse to the blood pulse and assists the heart in its operation.

It is, of course, possible to provide both control means 27, 28 and the control means 30, 31, 32 to control amplitude, frequency, and phase of the electrical pulses generated in the unit 11 and hence the pulses generated by the pump 13. Alternatively, either one of the control means may be eliminated.

The delivery of the reversed pressure pulses to the patient not only increases ventilation through the air passageways in which the wall has become inwardly displaced or collapsed, but also improve air or respiratory gas mixing in deeper regions of the lung so that, overall, the air or gas exchange is substantially improved. The apparatus is useful with patients in the chronic obstructive lung disease category, and also with patients having normal lungs but in respect of which artificial ventilation becomes necessary.

Figure 3:
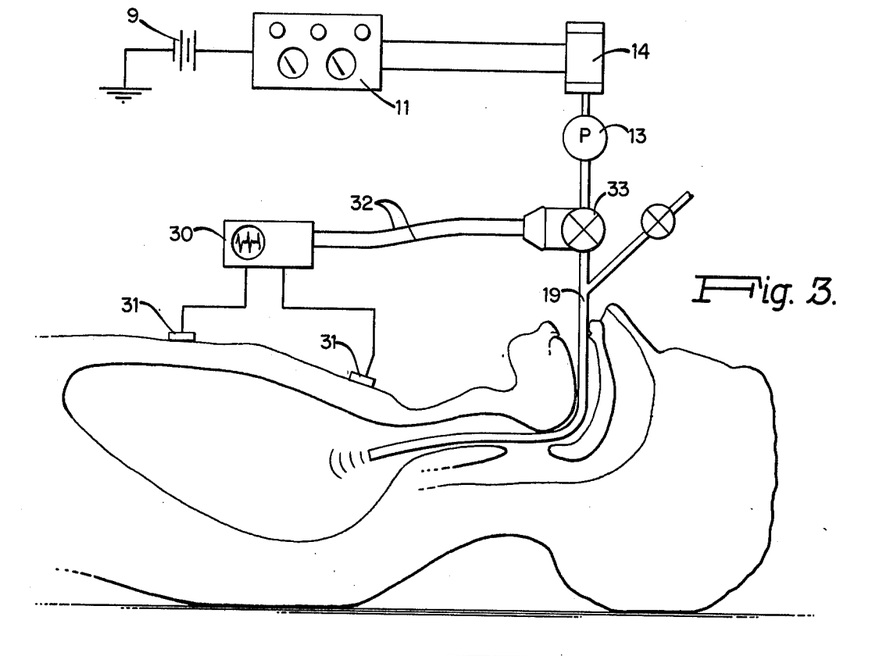
FIG. 3 illustrates the embodiment of FIG. 2 modified in respect of the manner in which the frequency and phase of the pressure pulses are controlled with reference to cardiac rhythm and omitting the artificial respiration means and the pleural pressure sensing means.

FIG. 3 illustrates a further embodiment of the apparatus which is functionally similar to that shown in FIG. 2. In this case, however, the pleural pressure sensing means and the artificial respiration means are omitted, and control of the frequency and the phase of the pressure pulses is effected by the interposition of an electrically operated valve 33 in the main duct 19.

The signal developed in the unit 30 may be used to open the valve 33 at a frequency corresponding to cardiac rhythm and by an amount, and at a time, such that the phase of the pressure pulses delivered down the duct 19 is optimally used to stimulate or assist heart operations, e.g., assist pulmonary blood circulation.

Figure 4:
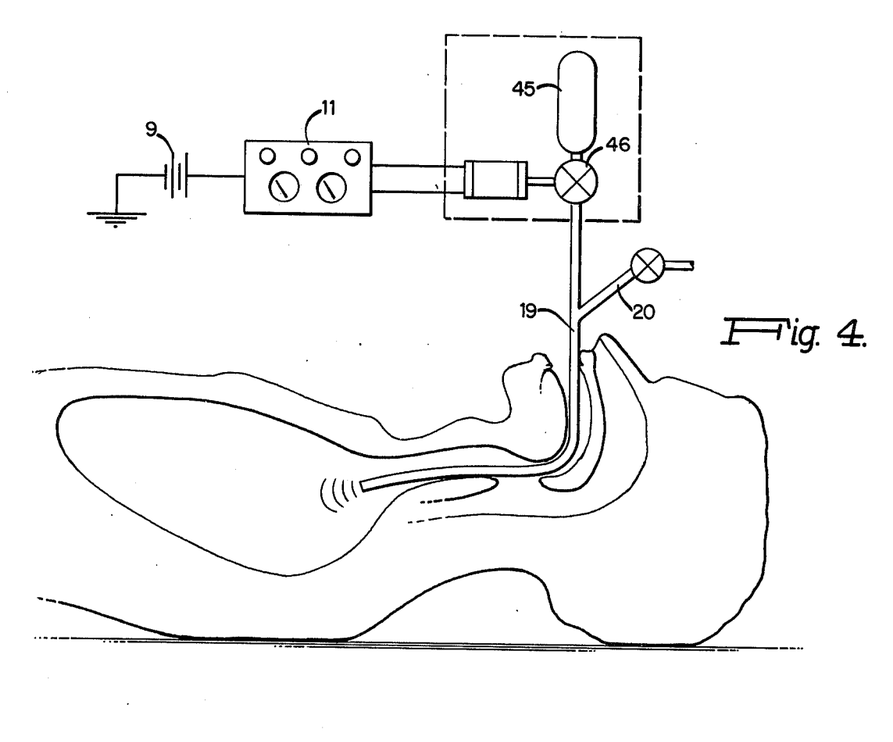
FIG. 4 illustrates a second embodiment of the invention wherein the pressure pulses are generated by releasing air from a pressurized reservoir.

Another embodiment of the invention, shown in FIG. 4, employs a means for producing the pressure pulses which differs from those of the previous embodiments, in that it comprises a reservoir chamber 45 which is pressurized with air or other respiratory gas which is releasable in the form of pressure pulses to the duct 19 under the control of a valve means 46. The valve means is electrically operated, e.g., by a solenoid, and is controlled by pressure pulses delivered from the unit 11.

Figures 5, 6:
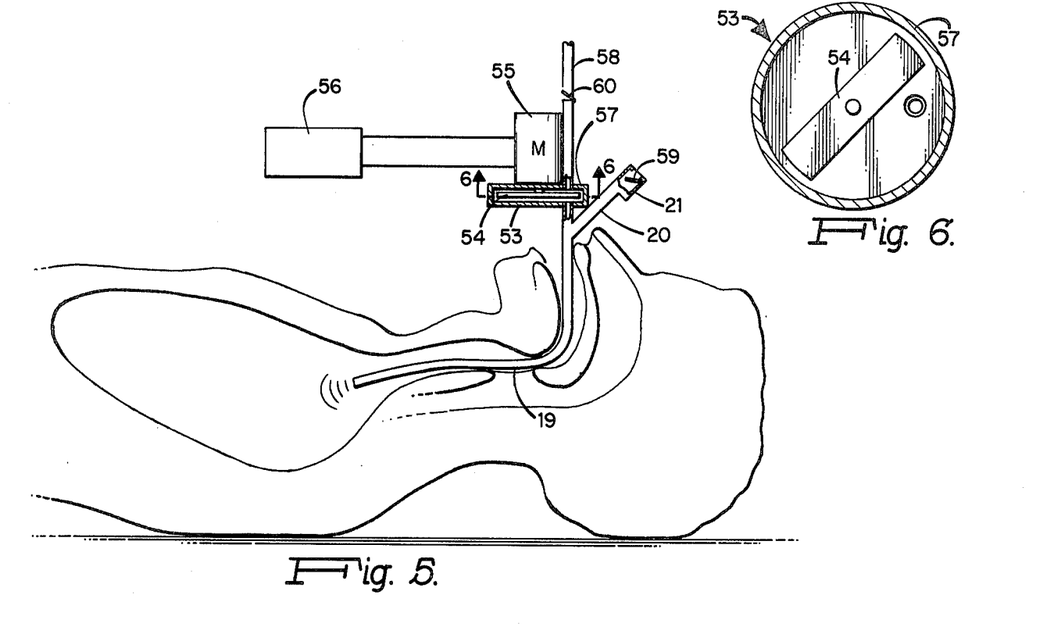
FIG. 5 illustrates a third embodiment of the invention wherein the pressure pulses are generated by reflection of air or other respiratory gas expired by the patient.
FIG. 6 is a cross-sectional view of the reflecting device of the apparatus of FIG. 5 taken on line 6—6 of FIG. 5.

In the embodiment illustrated in FIGS. 5 and 6, the means for generating the pressure pulses is passive rather than active, in that the energy source for the pressure pulses comprises the air or respiratory gas expired by the patient. The duct 19 contains a reflector means 53. This may be in the form of a plate element 54 which is rotated by a drive motor 55.

The reflector plate 54 rotates in a housing 57, one side plate of which has an opening over which the duct 19 is connected so that when either end portion or vane of the plate 54 is in alignment with the duct 19, there is reflection of any expiratory air travelling towards the outlet end 58 of the duct 19, whereas when either end or vane of the plate 54 is not in alignment with the duct, air flow towards the outlet 58 is unobstructed.

The reflections generate a series of pressure pulses which travel upstream of the duct 19 to the site of an obstruction in one or more air passageways of the patient's respiratory system as occurs in the use of the embodiments already described.

Inspired air is taken in through duct 20, the outlet 21 of which is controlled by a uni-directional valve 59 which prevents outflow of air so that all expired air passes along the main duct 19. Inspired air is not pulsed since the unidirectional valve 60 at the outlet 58 prevents intake of such air through the main duct 19.

Control of motor speed, and hence repetition frequency of pulses, and motor phase, and hence phase of the pulses, may be effected by providing a suitable control circuit in the unit 56 to which inputs can be fed, e.g, by means sensing cardiac rhythm.

In all the foregoing embodiments, the size of the duct 19 may be such that in addition to expiring air or respiratory gas through the duct, some air is also expired along parallel paths externally of the duct.

Figure 7:
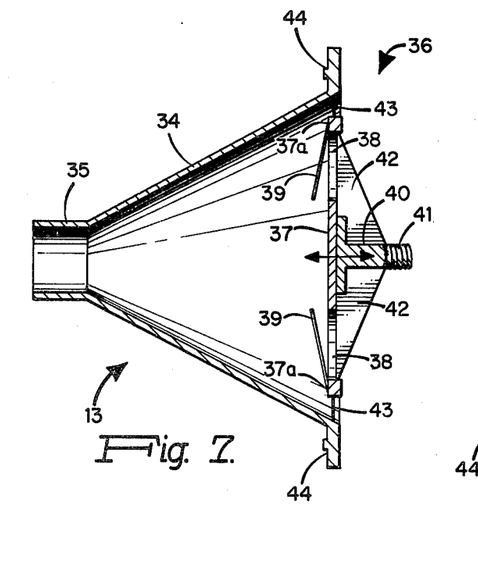
FIG. 7 is a view in side elevation and in vertical cross-section through one embodiment of a diaphragm type pump forming part of the pulse generating means which may be employed in the embodiment of FIG. 1, 2, or 3.
Figure 8:
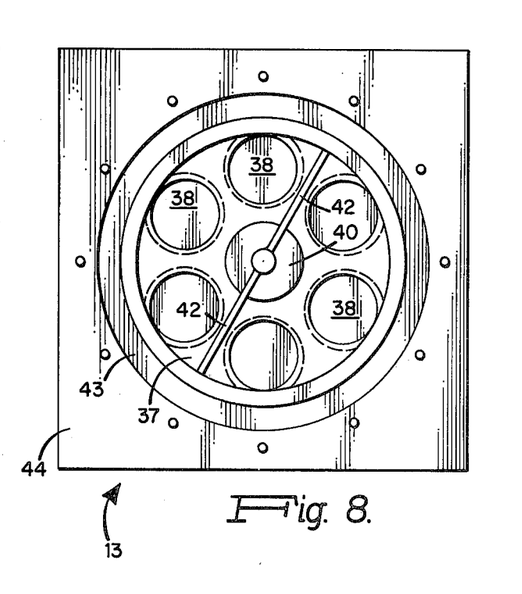
FIG. 8 is a view in end elevation of the pump shown in FIG. 7.

Referring now to FIGS. 7 and 8, a suitable constructional embodiment of the pump 13 is shown. The pump comprises an outlet chamber 34, which may be of frustoconical form as shown, terminating in an outlet fitting 35 for connection to the duct 19. At its other, larger diameter end, the structure is spanned by a diaphragm assembly 36.

The diaphragm assembly comprises a rigid circular plate 37 having a plurality of openings 38 extending therethrough and flap valve means 39 of a flexible material. The flap valve means 39 may comprise either individual flap elements associated with respective openings 38 or may be in the form of an annular member secured at its outer periphery to the marginal portion 37a of the plate 37 outwardly of the openings 38. Movement to the open position is effected as a result firstly of a difference in air pressure between the right and left-hand sides of the diaphragm assembly upon movement thereof from left to right as seen in the drawing, and secondly as a result of inertial forces.

Centrally, the plate 37 carries a driving spigot 40 which terminates in a screw-threaded portion 41 for connection to the driving element 41 (which may be a solenoid having an armature reciprocated axially and connected to the spigot 40). The stiffness of the diaphragm assembly may be maintained by webs 42 integral with, or secured to, the plate 37 between the openings 38 and secured to the driving spigot 40.

The plate 37 is mounted for axial movement relatively to the chamber 34 by a flexible diaphragm 43 secured respectively at its inner and outer margins to the plate 37 and an outwardly projecting flange 44 of the chamber 34. The diaphragm 43 may be made of elastic material for automatic restoration to a neutral or midposition from which it is displaced in either direction in response to energization of the driving solenoid by pulses from the unit 11.

When the plate 37 is driven forward, i.e., to the left, a positive pressure pulse is produced. During the backward stroke, i.e., to the right, because of the inertia, flap valve means 39 will open and the air pressure inside the chamber 34 will remain unchanged until the next forward stroke.

Figure 9:
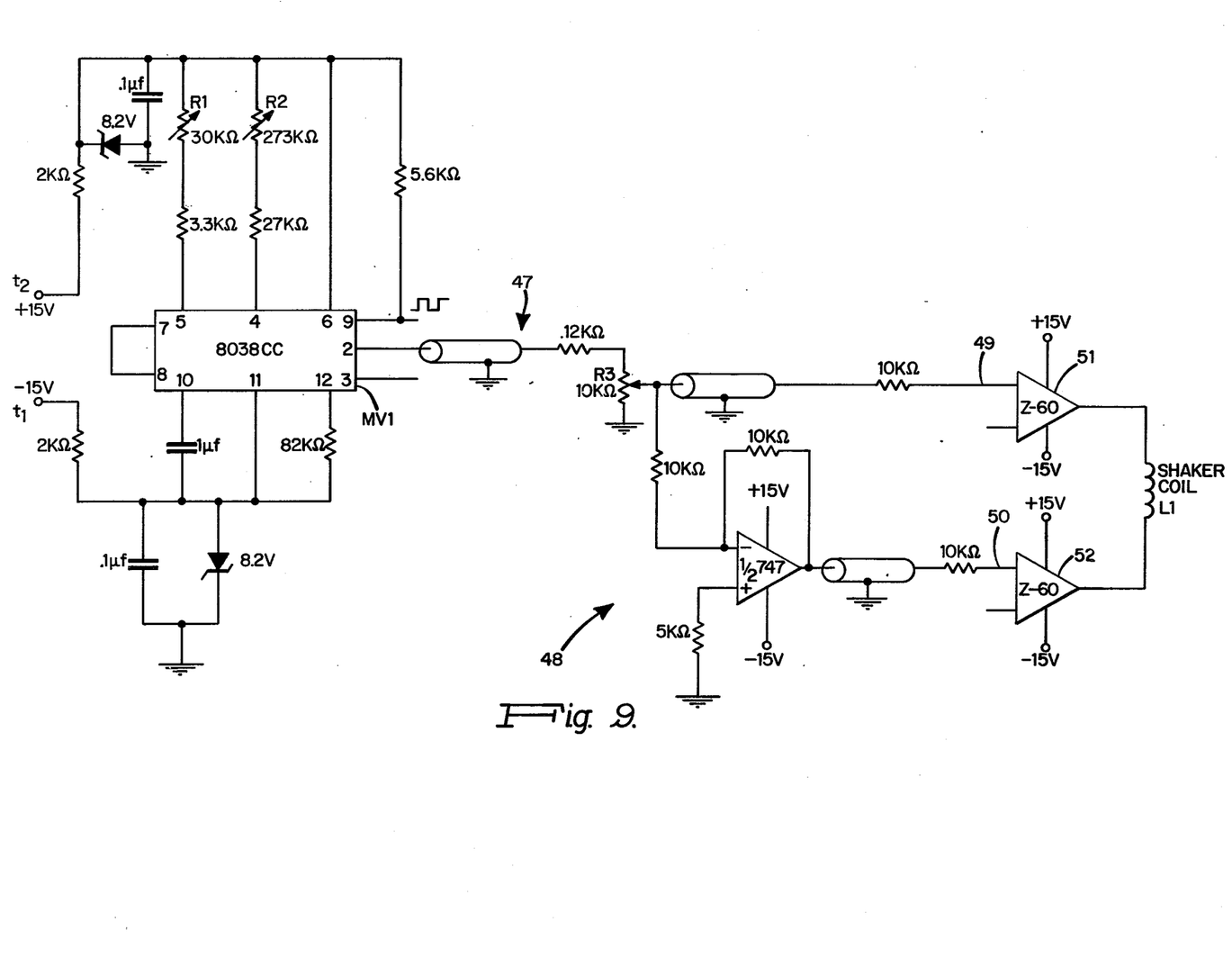
FIG. 9 is a circuit diagram of an electrical pulse generator for supplying driving pulses to an electrically actuated means for delivering pressure pulses of air or other respiratory gas.

FIG. 9 illustrates a suitable circuit which may be incorporated in the unit 11 for developing the series of electrical pulses.

An integrated circuit unit of the multi-vibrator type MV1 is powered from input terminals t1 connected to the source of current, such as the battery 9, and delivers pulses through a transmission line 47 to a phase splitter circuit 48. The phase splitter circuit develops outputs respectively on conductors 49 and 50 which are in anti-phase with respect to each other. These outputs are delivered to amplifiers 51, 52 connected to opposite ends of the operating coil L1 of the solenoid or device in the driving unit 14 which serves to operate the pump.

The integrated circuit unit MV1 provides for generation of two different wave forms, for example one having a fairly steep-sided symmetrical triangular shape and one approximating a sine wave.

These are combined to produce an output signal consisting of a train of pulses of which the leading half is derived from one of the two generated signals, and the trailing half from the other of these signals. Thus, if it is required to generate a saw tooth wave form in which the leading side rises gradually and the trailing side falls more steeply, it would be appropriate for the leading part to be formed from the leading part of the sine wave signal and the trailing part to be formed from the trailing half or part of the triangular signal. Resistors R1 and R2 may control the proportion (in time) of each of the primary signals utilized to develop the derived or output signal. Thus, by increasing both R1 and R2 proportionally, the length of each output pulse is increased and the repetition frequency of the pulse train is decreased. By varying either R1 or R2 individually, or both differently, the shape of each output pulse can be varied keeping either the repetition frequency constant or varying it as required.

It will be understood that if the driving means for the pump is as illustrated in FIG. 7 in which the leading side of each pressure pulse is generated by release of the plate 37, then the appropriate form of pulse will be one in which the release takes place suddenly, e.g. a saw tooth pulse having a gradually sloping leading edge and steeply sloping trailing edge would be appropriate. If, however, the pump were so arranged that the driving stroke of the pump to create the pulse took place in response to incidence of the pulse, as distinct from cessation of the pulse, then an appropriate form would be a pulse having a steeply rising leading edge, e.g. a saw tooth pulse in which the leading edge is steeper than the trailing edge.

Potentiometer R3 is adjustable to control the amplitude of the output pulses delivered from amplifiers 51, 52 to the coil L1.

In view of the foregoing, it may be seen that several objects of the present invention are achieved and other advantageous results have been attained.

As various changes could be made in the above construction without departing from the scope of the invention, it should be understood that all matter contained in the above description or shown in the accompanying drawings shall be interpreted as illustrative and not in a limiting sense.

I claim:

1. Apparatus for assisting expiration of respiratory gas through collapsed lung passageways, said apparatus comprising:

means for generating a series of pressure pulses having a waveform characterized by a rapid rise and gradual decline, having an amplitude sufficient, in combination with said waveform, to radially outwardly displace a collapsed lung passageway against the pleural pressure acting thereon, and having a frequency on the order of 15 Hz. such that successive pulses arrive at the passageway prior to its recollapse; and means for transmitting said generated pulses to said air passageway through exhaled respiratory gas in a direction opposite the direction of flow of said respiratory gas, whereby outward displacement of otherwise inwardly collapsed lung passageways is maintained and respiration is assisted.

2. The apparatus of claim 1 wherein said generating means comprises cyclically operable pump means.

3. The apparatus of claim 1 wherein said generating means comprises a reservoir of pressurized gas fitted with a cyclically operable gas release means.

4. The apparatus of claim 1 wherein said transmitting means comprises a main duct of a size sufficient for placement in the trachea, and a branch duct in fluid communication with said main duct.

5. The apparatus of claim 4 further comprising artificial respiration means in fluid communication with said branch duct.

6. The apparatus of claim 1 wherein said generating means comprises means for varying the amplitude of said pressure pulses whereby outward displacement of said gas passageway is optimized.

7. The apparatus of claim 1 wherein said generating means includes pleural pressure sensing means and pressure pulse amplitude control means responsive to the output of said pleural pressure sensing means for optimizing the outward displacement of said gas passageway.

8. The apparatus of claim 1 wherein said generating means comprises cardiac rhythm sensing means having an output signal and means for utilizing said output signal to control selected characteristics of said generated pressure pulses.

9. The apparatus of claim 8 wherein said means for utilizing said output signal comprises means for modulating the amplitude of said pressure pulses so that the amplitude reaches a maximum at a selected phase relationship to the cardiac rhythm.

10. The apparatus of claim 8 wherein said means for utilizing said output signal comprises means for controlling the incidence of pulses so that at least one pulse is generated at a selected phase relationship to the cardiac rhythm.

11. Apparatus for assisting the expiration of air from the lungs of a patient exhibiting the symptoms of emphysema, said apparatus comprising means for repetitively generating pressure pulses at a repetition rate on the order of 15 Hertz, said pulses being characterized by a relatively rapid rise in pressure followed by a relatively gradual decrease in pressure and by an amplitude sufficient to radially outwardly displace a collapsed lung passageway against the plural pressure acting thereon; and means, including a branch duct, for coupling said pressure pulses to the patient's bronchial passages, whereby, during exhalation, inner airways in the patient's lungs will be opened by said pulses, aiding the release of otherwise trapped air, thereby facilitating ventilation.

12. The apparatus of claim 11 further comprising means for controlling the phase of said pressure pulses.

13. The apparatus of claim 11 further comprising pressure pulse amplitude control means, pleural pressure sensing means operatively connected to a pressure transducer, and means for varying the amplitude of said pressure pulses in response to the output of said pressure transducer.

14. The apparatus of claim 11 further comprising means for sensing cardiac rhythm having an output signal and means for utilizing said output signal to control selected characteristics of said pressure pulses.

15. Apparatus for assisting the expiration of air from the lungs of a patient exhibiting the symptoms of emphysema, said apparatus comprising:

electrical signal source means for generating a repetitive sawtooth electrical waveform having relatively steep portions separated by relatively gradual portions, said waveforms being generated at a repetition rate on the order of 15 Hertz;

acoustic means including an electromagnetic transducer and a diaphragm assembly actuated by said transducer, said transducer being energized by said signal source to generate acoustic pressure pulses corresponding to said waveform and having an amplitude sufficient to radially outwardly displace a collapsed lung passageway against the pleural pressure acting thereon; and means, including a branch duct through which respiration takes place, for coupling said pressure pulses to the patient's bronchial passages, whereby, during exhalation, inner airways in the patient's lungs will be opened by said pulses, aiding the release of otherwise trapped air and thereby facilitating ventilation.

16. The apparatus of claim 15 wherein said diaphragm assembly comprises a chamber having a plate mounted for reciprocal movement in said chamber and connected to said electromagnetic transducer and flap valve means fixed in cooperative relation to said plate whereby pressure pulses are produced only upon movement of said plate in a single selected direction.

17. A process for assisting expiration of respiratory gas through collapsed lung passageways, said process being characterized by the steps of:

generating a series of pressure pulses having a waveform characterized by a rapid rise and gradual decline, having an amplitude sufficient, in combination with said waveform, to radially outwardly displace a collapsed lung passageway against the pleural pressure acting thereon, and having a frequency on the order of 15 Hz. such that successive pulses arrive at the passageway prior to its recollapse; and transmitting said generated pulses to said gas passageway through exhaled respiratory gas in a direction opposite the direction of flow of the respiratory gas, whereby outward displacement of otherwise inwardly collapsed lung passageways is maintained and respiration is assisted.

18. The process of claim 17 wherein said pressure pulses are generated by cyclically pumping a gas.

19. The process of claim 17 wherein said pressure pulses are generated by cyclically releasing quantities of pressurized gas contained in a reservoir.

20. The process of claim 17 wherein said pressure pulses are transmitted through a main duct of a size suitable for placement in a respiratory passage.

21. The process of claim 20 wherein said main duct is of a size sufficient for placement in the trachea and said process is further characterized by the step of passing all respiratory gases through said main duct.

22. The process of claim 21 wherein said respiratory gas is passed through said main duct via a branch duct in fluid communication with said main duct, said branch duct being situated to inhibit transmission of pressure pulses therethrough.

23. The process of claim 20 further characterized by the step of inducing artificial respiration through said main duct.

24. The process of claim 17 further characterized by the step of varying the amplitude of said generated pressure pulses to optimize the outward displacement of said gas passageway.

25. The process of claim 17 further characterized by the steps of sensing pleural pressure external to the lungs and utilizing said sensed pleural pressure to control the amplitude of said generated pressure pulses to optimize the outward displacement of said gas passageway.

26. The process of claim 17 further characterized by the steps of sensing cardiac rhythm and utilizing said sensed rhythm to control selected characteristics of said generated pressure pulses.

27. The process of claim 17 further characterized by controlling the frequency of said pressure waves on the order of 15 Hz.

28. A process for assisting expiration of respiratory gas through collapsed lung passageways, said process being characterized by the steps of:
  providing a main duct in fluid communication with a respiratory passage;
  artificially forcing respiratory gas into and out of the lungs through said duct;
  generating a series of pressure pulses at a frequency on the order of 15 Hz having a waveform characterized by a rapid rise and gradual decline, and having an amplitude sufficient, in combination with said waveform, to radially outwardly displace a gas passageway in the lungs against the pleural pressure acting thereon; and
  transmitting said generated pulses through said duct and to the site of said collapsed lung passageway through exhaled respiratory gas, whereby outward displacement of otherwise inwardly collapsed lung passageways is maintained and respiration is assisted.

29. The process of claim 28 wherein said respiratory gas comprises a gas used in anaesthesia.

* * * * *